(12) United States Patent
Tets et al.

(10) Patent No.: US 8,987,277 B2
(45) Date of Patent: Mar. 24, 2015

(54) FUNGICIDE

(75) Inventors: Viktor Veniaminovich Tets, Saint-Petersburg (RU); Georgy Viktorovich Tets, Saint-Petersburg (RU); Viktor Iosifovich Krutikov, Saint-Petersburg (RU)

(73) Assignees: Viktor Veniaminovich Tets, Saint Petersburg (RU); Georgy Viktorovich Tets, Saint Petersburg (RU)

( * ) Notice: Subject to any disclaimer, the term of this patent is extended or adjusted under 35 U.S.C. 154(b) by 0 days.

(21) Appl. No.: 13/991,477

(22) PCT Filed: Mar. 3, 2011

(86) PCT No.: PCT/RU2011/000140
§ 371 (c)(1),
(2), (4) Date: Jun. 4, 2013

(87) PCT Pub. No.: WO2012/078070
PCT Pub. Date: Jun. 14, 2012

(65) Prior Publication Data
US 2013/0261301 A1 Oct. 3, 2013

(30) Foreign Application Priority Data
Dec. 6, 2010 (RU) ................................ 2010149979

(51) Int. Cl.
*A01N 43/54* (2006.01)
*C07D 239/02* (2006.01)
*C07D 239/545* (2006.01)

(52) U.S. Cl.
CPC ............ *A01N 43/54* (2013.01); *C07D 239/545* (2013.01)
USPC .......................................... 514/256; 544/311

(58) Field of Classification Search
CPC .................................................. C07D 239/545
See application file for complete search history.

(56) References Cited

U.S. PATENT DOCUMENTS

| 3,361,745 A | 1/1968 | Schroeder |
| 6,730,787 B1 | 5/2004 | Krutikov et al. |

FOREIGN PATENT DOCUMENTS

| RU | 2 198 166 | 2/2003 |
| RU | 2198166 C2 | 2/2003 |
| RU | 2 260 590 | 9/2005 |
| RU | 2260590 C1 | 9/2005 |
| WO | WO 00/34250 | 6/2000 |
| WO | WO 2005/103014 | 11/2005 |

OTHER PUBLICATIONS

Krutikov, V.I., et al. "5-Arylideneaminouracils: II. Synthesis of Sodium and Ammonium Salts." Russian Journal of General Chemistry. (2009), vol. 79, No. 5, pp. 991-995.*
Group 1: Alkali Metals. Available from: < http://web.archive.org/web/20080410115147/http://www.rsc.org/chemsoc/visualelements/pages/data/intro_groupi_data.html >. Published: Apr. 10, 2008.*
Berkengeim et al. "Chemistry and Technology of Synthetic Drugs" The Main Edition of the Chemical Literature, Moscow, 1935.
Extended European Search Report dated Jun. 11, 2014, which issued during prosecution of European Application No. 11847307.3, which corresponds to the present application.
International Search Report dated Aug. 25, 2011, which issued during prosecution of International Application No. PCT/RU2011/000140, which corresponds to the present application.
International Preliminary Report on Patentability dated Jan. 18, 2013, which issued during prosecution of International Application No. PCT/RU2011/000140, which corresponds to the present application.
Krutikov et al. "5-Arilidenaminouratsily. I. Sintez, vliyanie fiziko-khimicheskikh parametrov na uroven biologicheskoy aktivnosti" Zhurnal obschey khimii, 2009, 79(5), pp. 813-818.
Tyukavkina et al., "Bioogranicheskaya khimiya" Moscow <<Drofa>> 2005, pp. 304-305.
Written Opinion of the International Searching Authority dated Aug. 25, 2011, which issued during prosecution of International Application No. PCT/RU2011/000140, which corresponds to the present application.
Krutikikov V.I., et al. 5-Arilidenaminouratsily. I. Sintez, vliyanie fiziki-khimicheskikh parametrov na uroven biologicheskoy aktrivnosti. Zurnal obschey khimi St. Peterspur, (c) 2009.
Tyukabikina N.A., et al., Biogranicheskaya khimiya Moskow ,<<Drofa>>2005m o, 304-305, (c) 2005.

* cited by examiner

Primary Examiner — Andrew D Kosar
Assistant Examiner — John S Kenyon
(74) Attorney, Agent, or Firm — Troutman Sanders LLP

(57) ABSTRACT

The invention relates to fungicides and can be used for treating diseases caused by fungi, and also for preventing damage to various materials and agricultural products by fungi. The fungicide is a 2,4-dioxo-5-(2-hydroxy-3,5-dichlorobenzylidene)amino-1,3-pyrimidine salt of general formula: (A) or a dimer thereof: (B), where X is selected from the series consisting of: $Na^+$, $K^+$, $Li^+$ and $NH_4^+$. An effective preparation having anti-fungal activity with a broad spectrum of action is created.

18 Claims, 1 Drawing Sheet

FUNGICIDE

TECHNICAL FIELD

The invention relates to fungicides and can be used for treating diseases caused by fungi, and also for preventing damage to various materials and agricultural products by fungi.

BACKGROUND ART

One of the most serious problems of modern medicine, veterinary science and plant growing is known to consist in fungus, bacterial and viral diseases, many of which are extremely difficult to combat. Said difficulty is due to insufficient effectiveness of existing preparations and the fast variability of microbes that leads to creation of resistant forms, see Fidel P. L. Jr, Vazquez J. A., Sobel J. D. *Candida glabrata*: review of epidemiology, pathogenesis and clinical disease with comparison to *C. albicans* 1999, 1:80-96. White T. Antifungal drug resistance in *Candida albicans* ASM News 8:427-433.

Similar problems persist in veterinary science and in the industry, where damage to products caused by development and propagation of micro-organisms is very common. The most widely known preparations for treating fungus diseases are nystatin, amphotericin B, fluconazole and terbinafine (Encyclopaedia of drugs RLS-2009, RLS (Registry of Medicines of Russia), 2009, Moscow, p. 928). However, each of abovementioned preparations has certain disadvantages. Although fluconazole has a broad spectrum of activity, its effect is mainly fungistatic [Pharmaceutical microbiology. Ed. by W. B. Hugo and A. D. Russel Blackwell Scientific Publications, Oxford, 1987, 511 p]. Fluconazole is also used for preventing damage to plants and agricultural products by fungi. Fluconazole is also known to be used in archiving for the treatment of paper. Terbinafine does not destroy yeast-like fungi. The abovementioned facts make it extremely difficult to use said preparations for treating patients with weakened immune system. Nystatin is another popular preparation. Its main disadvantage consists in its low activity against multicellular fungi. The most active anti-fungal preparation is amphotericin B, however, it is extremely toxic and is poorly tolerated by patients during treatment of various mycoses.

The fluconazole preparation—2-(2,4-difluorophenyl)-1,3-bis(1N-1,2,4-triazol-1-yl)-2-propanol) was taken as a prototype of the present invention.

SUMMARY OF THE INVENTION

The object of the invention is to create an effective preparation having anti-fungal activity with a broad spectrum of action.

According to the invention there is provided a fungicide created through synthesis, which is a 2,4-dioxo-5-(2-hydroxy-3,5-dichlorobenzylidene)amino-1,3-pyrimidine salt of general formula:

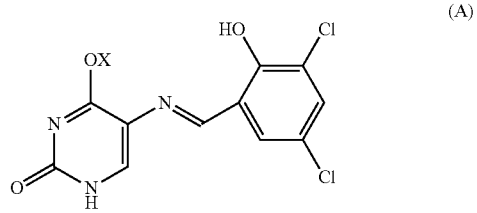

(A)

or a dimer thereof:

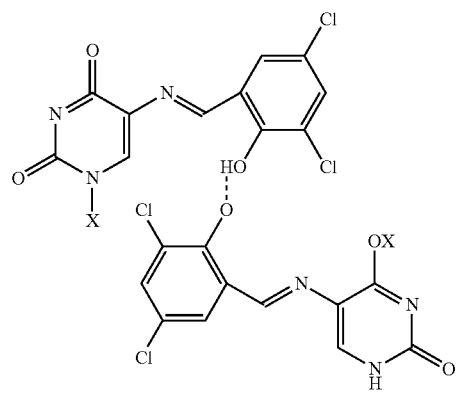

(B)

where X is selected from the series consisting of: $Na^+$, $K^+$, $Li^+$ and $NH_4^+$.

The applicant has not found any sources of information containing data on technical solutions identical to the present invention, which enables to conclude that the invention conforms to the criterion "Novelty" (N).

The applicant has not found any sources of information containing data on the influence of the features of the invention on the technical result produced by their implementation. In applicant's opinion, this enables to conclude that the present technical solution conforms to the criterion "Inventive Step" (IS).

BRIEF DESCRIPTION OF THE DRAWINGS

The invention is further explained, by way of example, with reference to the following drawings, in which.

PREFERRED EMBODIMENT

Figure 1:
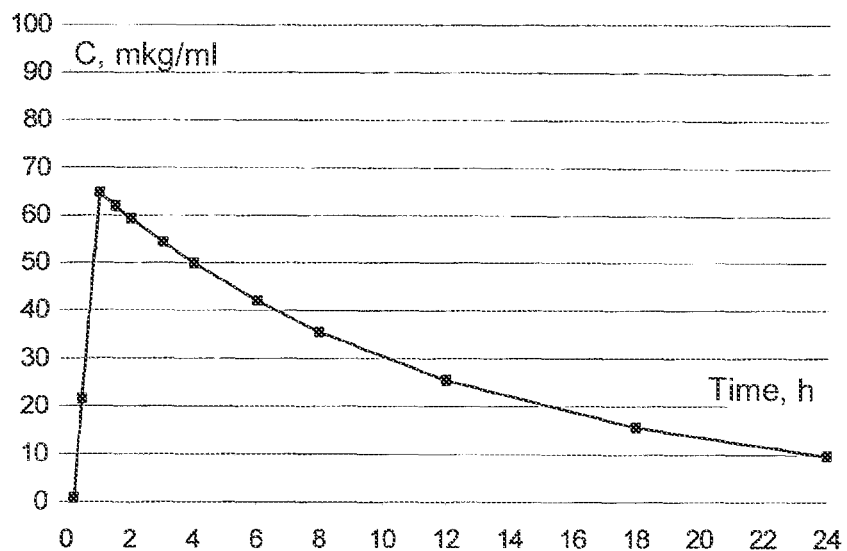
FIG. 1 shows averaged dynamics of concentration of the inventive substance in blood plasma of experimental animals after administering the inventive substance (forms A and B) in the form of vaginal suppositories.
Figure 2:
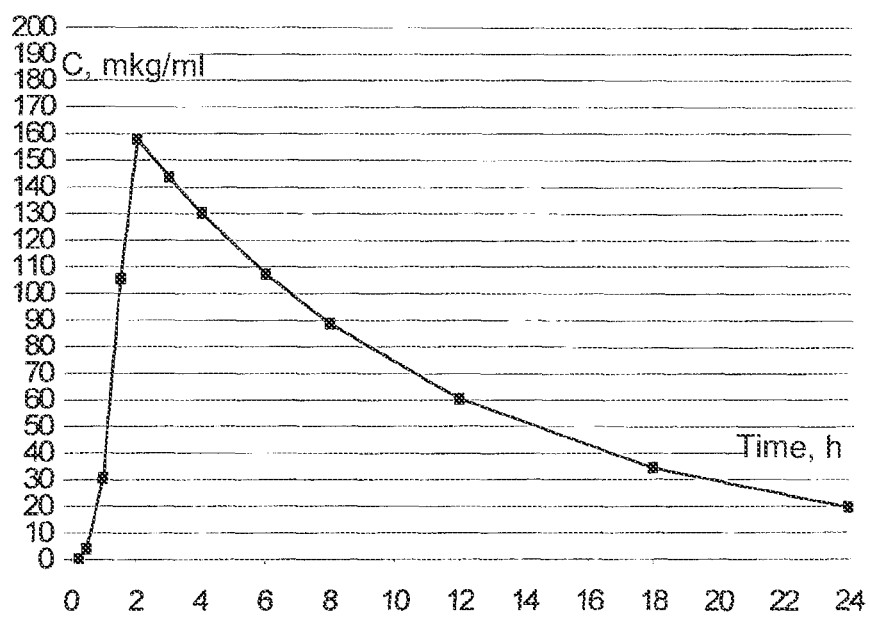
FIG. 2 shows averaged pharmacokinetic curves of the inventive substance concentration in blood plasma of the experimental animals during oral administration in the form of capsules.

Synthesis of the Inventive Substance.

7 g of caustic soda (0.175 mol) diluted in 350 ml of water were added to 21.5 g of 5-aminouracil (0.17 mol). The mixture was heated at a boiling water bath until 5-aminouracil was fully dissolved. Then 32 g of 3,5-dichlorosalicylic aldehyde (0.17 mol) dissolved in 150 ml of hot ethanol were added in portions to the reaction mass at the temperature of the boiling water bath while stirring. For the purpose of quantitative transfer of aldehyde into the reaction flask, the vessel in which it was dissolved was washed with 50 ml of ethanol. A sediment of orange-red color precipitated in the flask. Then the reaction mass was stirred for 30 more minutes at the water bath and was gradually cooled down to room temperature. The obtained residue was filtered, washed with 300 ml of ethanol and dried. 600 ml of aqueous ethanol were distilled off the filtrate by means of rotary evaporator. The remaining mixture was filtered by means of glass filter to obtain 75.5 g of the target compound.

The output of the target product was 98% from the theoretically possible output.

Potassium, lithium and aluminum salts of 2,4-dioxo-5-(2-hydroxy-3,5-dichlorobenzylidiene)amino-1,3-pyrimidine are obtained in a similar way.

Dimer of sodium salt of 2,4-dioxo-5-(2-hydroxy-3,5-dichlorobenzylidiene)amino-1,3-pyrimidine is obtained in the following way.

0.4 g of caustic soda and 100 ml of 90% ethanol were placed into a flask. The mixture was heated at 40° C. until the caustic soda was fully dissolved. Then the reaction mass was cleaned from undissolved sodium carbonate and sodium chloride by means of filtration. 12.7 g of 5-aminouracil were added in portions to the obtained solution at 40° C. The obtained reaction mass was stirred at boiling water bath until aminouracil was fully dissolved. At the same time, 19.1 g of 3,5-dichlorosalicylic aldehyde were dissolved in 400 ml of 90% ethanol. The obtained solution was added drop-wise to a solution of sodium salt of 5-aminouracil while stirring at temperature of boiling water bath. A sediment of orange-red color began to precipitate almost immediately. After adding the whole volume of alcoholic solution of aldehyde, the reaction mass was heated for 0.5 h more at boiling water bath. After the reaction mass was cooled down to room temperature, the sediment was filtered, washed with 100 ml of 96% ethanol and dried. The output of the target product was 98%.

Dimers of other salts of 2,4-dioxo-5-(2-hydroxy-3,5-dichlorobenzylidiene)amino-1,3-pyrimidine are obtained in a similar way.

Various solutions and other forms prepared on the basis of the inventive fungicide are used for fighting the fungi.

Pharmaceutical compounds for treating diseases caused by fungi that can be manufactured from the inventive substance include pharmaceutically acceptable salts thereof, pharmaceutically acceptable fillers, adjuvants and transporters. Substances that can be used in compounds with the inventive substance can include polyvinylpyrrolidone, methylcellulose, oxypropylmethylcellulose, carboxymethylcellulose, sodium carboxymethylcellulose and some other substances: corn starch, talcum, kaolin, bentonites, aerosil, beet sugar, milk sugar, sodium chloride, sodium bicarbonate and some others.

Pharmaceutically acceptable salts, pharmaceutically acceptable filler, adjuvant or transporter can include exchangeable ions, aluminum oxide, aluminum stearate, lecithin, serum proteins, buffer solutions such as phosphates, glycine, sorbic acid, potassium sorbate, partial mixture of glycerides of saturated vegetable fatty acids, water, salts and electrolytes, such as protamine sulfate, $Na_2HPO_4$, $K_2HPO_4$, sodium chloride, salts of zinc, colloid silicon dioxide, trisilicate of magnesium, polyvinyl pyrrolidone, polyethylene glycol, carboxymethylcellulose of sodium, wax, polyethylene-polypropylene block polymers and lanoline.

Pharmaceutical preparations containing the inventive substance can be administered orally, parenterally by means of a spray, locally, through rectum, nasally, lingually, vaginally or by means of implants.

Pharmaceutical agents based on the invention can be manufactured as a sterile preparation for injections, both as an aqueous solution and an oil suspension. Said suspension can be created by means of a known method employed for producing such forms of drugs, using any suitable detergents and other auxiliary substances (Tween 80). Any non-toxic parenterally acceptable substance, e.g. 1,3-butanediol, can be used as a solvent or liquid base for the sterile preparation produced as a solution or a suspension. Mannitol, water, Ringer's solution and isotonic solution of sodium chloride can be used as acceptable transporters and solvents. In order to create an oily solution of the substance one must use non-volatile vegetable oils that are traditionally used for obtaining oily solutions or suspensions. Any neutral non-volatile oil is suitable for this purpose, including synthetic mono- and diglycerides, as well as fatty acids. For creation of injection preparations one can use oleic acid and glycerides, olive or castor oil, in particular their polyoxyethylated derivatives. The oily solutions and suspensions can also comprise long-chain alcohols or other similar substances as stabilizers and detergents.

Pharmaceutical preparations based on the invention can be administered orally, in any dosage and form acceptable for oral administration, including capsules, pills, aqueous solutions and suspensions. For pills, lactose and corn starch can be used as fillers. Magnesium stearate can be used as a process additive. If the preparation for oral administration is manufactured as a capsule, then lactose and corn starch are used as fillers. If the drug is manufactured as an aqueous suspension, then one can add to the active substance various emulsifiers and agents that provide the medicine with sweet taste, pleasant odor and color.

Pharmaceutical preparations based on the invention can be prescribed as suppositories for rectal or vaginal administration. These drug forms can be manufactured by mixing the inventive substance with a suitable non-irritant filler that remains hard in room temperature and becomes soft in rectal or vaginal temperature. Cocoa butter, beeswax and polyethylene glycols can be used as fillers.

In preparations intended for skin application, the active substance should be combined with a suitable ointment base that can contain the active substance in dissolved form or as a suspension. Ointment base can include mineral oils, liquid petrolatum, white petrolatum, propylene glycol, a mixture of polyoxyethylene and polyoxypropylene, emulsifying wax and water, as well as various creams. Pharmaceutical preparations based on the inventive substance can also be used for lower bowel segments in the form of rectal suppositories or any other suitable form of medicine.

The inventive substance can also be used for manufacturing such medical forms for external use as plasters, nasal sprays or inhalers. Such medical forms can be manufactured by means of already existing technologies that are used for manufacturing such forms. Liquid phase for dissolving the inventive substance can be embodied as isotonic solution of sodium chloride (physiological solution); stabilizer can be embodied as benzyl alcohol or any other suitable substance; absorption activator can be embodied as fluorocarbons in order to increase the bioavailability.

Preparation prepared on the basis of the inventive substance can be used in doses from 0.01 to 25 mg of the active substance per 1 kilogram of patient weight, from 1 to 5 times per 24 hours.

Prolonged forms with boosted action of the active substance can be obtained on the basis of liposomes or complexes with polylactic acid.

The inventive fungicide substance also can be used for treating animals and for fighting fungi that damage various materials, agricultural crops and products.

Examples of studies of the biological activity of preparations manufactured on the basis of the inventive fungicide substance.

EXAMPLE 1

Discovering the Minimum Inhibiting Concentration of the Inventive Substance (Forms A and B) Towards Unicellular Fungi Fungi were grown in Sabouraud's agar. The effect of the substance was assessed by means of the serial dilution method.

The obtained data show that the activity of the inventive agent is higher than that of the preparation used for comparison.

EXAMPLE 2

Discovering the Minimum Inhibiting Concentration of the Inventive Agent Towards Multicellular Fungi The obtained data demonstrate high activity of the inventive agent, which is significantly higher than the activity of the preparation used for comparison.

EXAMPLE 3

Assessment of the Fungicide Effect

Strains of fungi of *Candida* genus (*Candida albicans* strain 15) that are resistant towards disinfecting agents and *trichophyton* (*Trichophiton gypseum*), which were cultivated in Sabouraud's agar, were used as test microorganisms.

Forms A and B were dissolved in sterile distilled water.

The method of serial dilutions in microplates was used in the experiment. The dissolved substance was titrated in the culture medium, then the test microorganisms were introduced and after certain intervals of disinfection time the neutralizer was added, namely 0.1% solution of citric acid. After the exposure during 1-2 minutes the contents of each well were plated to solid culture media.

The following concentrations of the substance were studied: 0.1-0.05-0.025-0.0125% of the drug for action duration of 1, 3, 5, 10, 20, minutes and 1.0-1.5-3.0 and 24 h.

All inoculations were incubated at an optimum temperature during 24 hours.

The fungicide effect was assessed according to the presence or absence of growing microorganisms in the culture media.

The following results were obtained: the inventive substance in forms A and B destroys fungi of *trichophyton* genus in concentration of 0.1% and *Candida* genus in concentration of 0.025% at the exposure time of 24 h.

The preparation that was used for comparison did not destroy the microbes under the abovementioned conditions. Said fact supports the data that show that the preparation used for comparison has only fungistatic effect.

EXAMPLE 4

Study of Concentration of the Inventive Substance in Blood Plasma of Experimental Animals After Administering the Inventive Substance (Forms A and B) in the Form of Vaginal Suppositories Averaged dynamics of concentration C of the inventive substance, for both A and B forms, in blood plasma of experimental animals after vaginal administration of the preparation (in linear coordinates) does not depend on the form (A or B).

Dispersion of individual values was moderate: coefficient of variation CV amounted to 18-42%.

Therefore, vaginal administration of the substance provides not only local effect, but also ensures introduction of the substance into the general blood circulation.

EXAMPLE 5

Concentration of the Inventive Substance in Blood Plasma of Experimental Animals During Oral Administration in the Form of Capsules Results of measurements of concentration C of the substance in blood plasma of rabbits during oral administration (capsules of 0.15 g) are shown in the Figure in the form of averaged pharmacokinetic curves, and they do not depend on the form of the inventive substance.

After administration the substance began to enter the general blood circulation after approximately 15 minutes; after 2 hours the concentration of the substance in the blood reached its maximum (approximately 160 µg/ml); then it was gradually removed from the organism and 24 hours after its administration the detected presence of the substance in blood plasma was minimal (approximately 20 µg/ml). Dispersion of individual values was moderate: coefficient of variation CV amounted to 8-22%.

EXAMPLE 6

Effect of the Inventive Fungicide on Fungi that Cause Diseases in Plants and Damage Agricultural Products Various fungi were used in the experiment—vegetative forms and spores of *Alternaria alternata, Fusarium moniliforme, Botrytis* spp. that cause diseases of plants and damage agricultural products.

Biocidal properties were tested on spores of fungi cultures with optical density of the inoculated dose p E=0.310.

EXAMPLE 7

Effect of the Inventive Fungicide on Fungi that Damage Paper, Wood and Dyes Thereof Various fungi were used in the experiment—vegetative forms and spores of *Aspergillis niger, Penicillium ochro-chloron* that damage paper, wood and dyes thereof.

Biocidal properties were tested on spores of fungi cultures with optical density of the inoculated dose p E=0.310.

The provided examples confirm high activity of the inventive fungicide in both forms (2,4-dioxo-5-(2-hydroxy-3,5-dichlorobenzylidiene)amino-1,3-pyrimidine salt or a dimer thereof) towards fungi that cause diseases of animals and plants, and damage agricultural products and various materials.

Therefore, the results of studies of the inventive substance demonstrated that it has broad-spectrum antifungal activity, affects unicellular and multicellular fungi and spores thereof (trichophytons and aspergilli), affects strains that are resistant towards disinfectants and has fungicidal effect. The substance has not only local effect but also enters the general blood circulation in various forms of administration.

INDUSTRIAL APPLICABILITY

The invention can be implemented by means of known materials and equipment. In applicant's opinion, this enables to conclude that the invention conforms to the criterion "Industrial Applicability" (IA).

Results of Discovering the Minimum Inhibiting Concentration of the Inventive Substance (Forms A and B) Towards Unicellular Fungi

TABLE 1

| Substance | Minimum inhibiting concentration (μg/ml) | | | | |
|---|---|---|---|---|---|
| | C. albicans | C. glabrata | C. krusei | C. parapsilosis | S. cerevisiae |
| Fluconazole | 2 | 64 | 32 | 0.250 | 0.125 |
| A | 1 | 0.125 | 1 | 0.250 | 0.125 |
| B | 1 | 0.250 | 1 | 0.125 | 0.125 |

Results of Discovering the Minimum Inhibiting Concentration of the Inventive Agent Towards Multicellular Fungi

TABLE 2

| Type of multicellular fungi | Minimum inhibiting concentration (MIC, μg/ml) | | |
|---|---|---|---|
| | Fluconazole | A | B |
| Aspergillus | 64 | 2 | 2 |
| Mucor | 64 | 1 | 1 |

Effect of the Inventive Fungicide on Fungi that Cause Diseases in Plants and Damage Agricultural Products

TABLE 3

| Fungi spores (a mixture) | Minimum inhibiting (biocidal) concentration of the substance (μg/ml) | | |
|---|---|---|---|
| | A | B | Fluconazole |
| A. alternata | 4.0 | 2.0 | 32 |
| F. moniliforme | 8.0 | 4.0 | 64 |
| Botrytis spp | 8.0 | 4.0 | 64 |

Effect of the Inventive Fungicide on Fungi that Damage Paper, Wood and Dyes Thereof

TABLE 4

| Fungi spores (a mixture) | Minimum inhibiting (biocidal) concentration (MIC) of the substance (μg/ml) | | |
|---|---|---|---|
| | A | B | Fluconazole |
| Aspergillis niger | 2.0 | 1.0 | 64 |
| Penicillium ochro-chloron | 8.0 | 4.0 | 64 |

The invention claimed is:

1. A compound of formula:

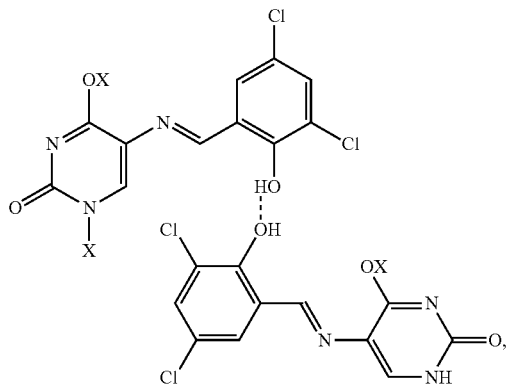

wherein:
X is selected from the group consisting of: Na$^+$, K$^+$, Li$^+$ and NH$_4^+$; and
a dotted line is a hydrogen bond.

2. The compound of claim 1, wherein X is Na$^+$.
3. The compound of claim 1, wherein X is K$^+$.
4. The compound of claim 1, wherein X is Li$^+$.
5. The compound of claim 1, wherein X is NH$_4^+$.
6. A composition comprising the compound of claim 1, and one or more excipients.
7. A composition comprising a compound of formula:

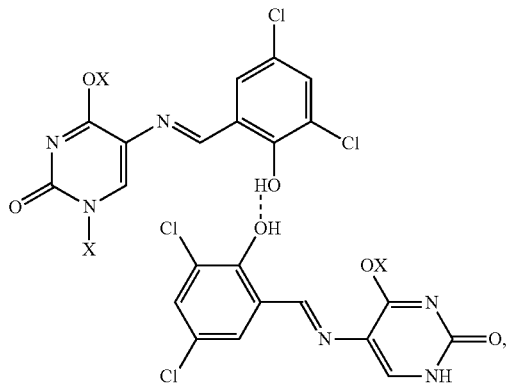

prepared by the process of:
providing a solution comprising XOH and ethanol at a temperature of at least about 40° C.;
adding 5-aminouracil to said solution to afford a reaction mixture;
heating said reaction mixture to a temperature of at least about 100° C.;
adding 3,5-dichlorosalicylic aldehyde to said heated reaction mixture; and
isolating the resulting composition,
wherein:
X is selected from the group consisting of: Na$^+$, K$^+$, Li$^+$ and NH$_4^+$; and
a dotted line is a hydrogen bond.

8. The composition of claim 7, wherein X is Na$^+$.
9. The composition of claim 7, wherein X is K$^+$.
10. The composition of claim 7, wherein X is Li$^+$.
11. The composition of claim 7, wherein X is NH$_4^+$.

12. A method of preparing a composition comprising a compound of formula:

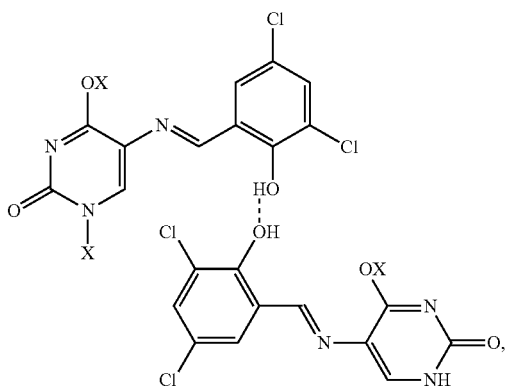

comprising:
  providing a solution comprising XOH and ethanol at a temperature of at least about 40° C.;
  adding 5-aminouracil to said solution to afford a reaction mixture;
  heating said reaction mixture to a temperature of at least about 100° C.;
  adding 3,5-dichlorosalicylic aldehyde to said heated reaction mixture; and
  isolating the resulting composition,
wherein:
  X is selected from the group consisting of: $Na^+$, $K^+$, $Li^+$ and $NH_4^+$; and
  a dotted line is a hydrogen bond.

13. The method of claim 12, wherein said solution comprising XOH and ethanol is heated at 40° C. until XOH is fully dissolved.

14. The method of claim 12, wherein said solution comprising XOH and ethanol is filtered to remove undissolved salts before adding 5-aminouracil to said solution.

15. A method for preventing or inhibiting growth of a fungus comprising administering an effective amount of the compound of claim 1.

16. A method for treating a fungal infection in a subject in need thereof comprising administering to the subject an effective amount of the compound of claim 1.

17. A method for preventing or inhibiting growth of a fungus comprising administering an effective amount of the composition of claim 7.

18. A method for treating a fungal infection in a subject in need thereof comprising administering to the subject an effective amount of the composition of claim 7.

* * * * *

UNITED STATES PATENT AND TRADEMARK OFFICE
CERTIFICATE OF CORRECTION

PATENT NO. : 8,987,277 B2
APPLICATION NO. : 13/991477
DATED : March 24, 2015
INVENTOR(S) : Viktor Veniaminovich Tets, Georgy Viktorovich Tets and Viktor Iosifovich Krutikov It is certified that error appears in the above-identified patent and that said Letters Patent is hereby corrected as shown below:

In the Claims

Column 8, Lines 5-20: In Claim 1, please replace the structure:

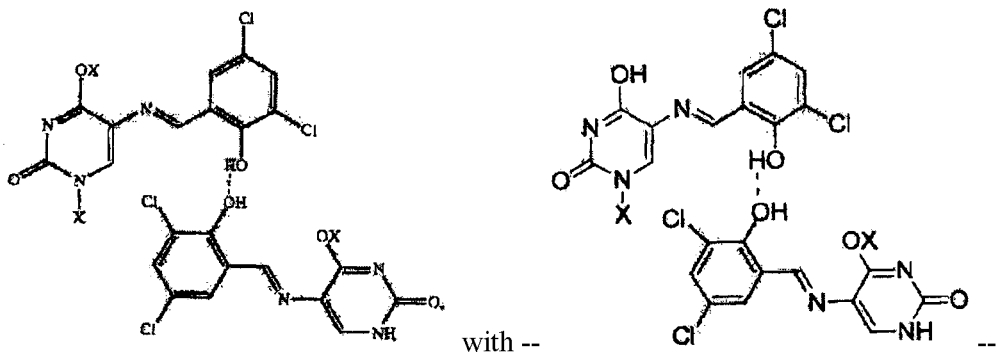

Column 8, Lines 39-49: In Claim 7, please replace the structure:

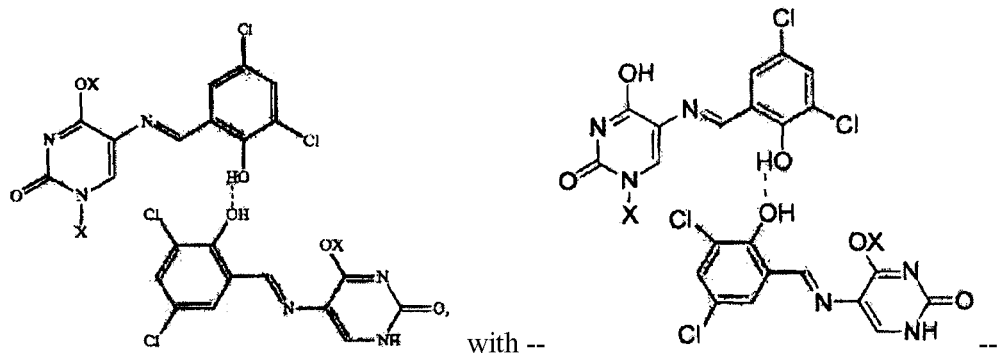

Signed and Sealed this
Seventh Day of July, 2015

Michelle K. Lee
*Director of the United States Patent and Trademark Office*

CERTIFICATE OF CORRECTION (continued)
U.S. Pat. No. 8,987,277 B2

Column 9, Lines 5-20: In Claim 12, please replace the structure:

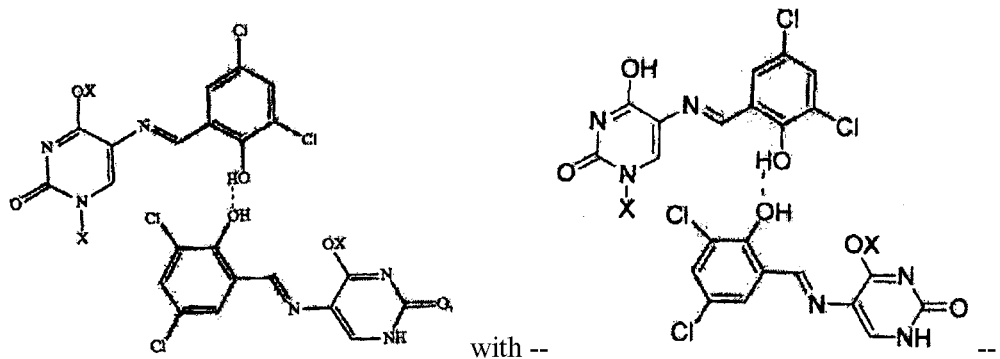 with --